United States Patent [19]

Metcalf

[11] Patent Number: 5,163,839
[45] Date of Patent: Nov. 17, 1992

[54] DIRECT BOND RETAINER FOR TEETH

[76] Inventor: Lyman R. Metcalf, 2155 N. 200 West, Provo, Utah 84604

[21] Appl. No.: 734,436

[22] Filed: Jul. 23, 1991

[51] Int. Cl.⁵ .............................................. A61C 3/00
[52] U.S. Cl. ........................................... 433/6; 433/9
[58] Field of Search ..................... 433/6, 8, 9, 10, 11, 433/18, 20, 21, 172, 178, 181, 182, 215

[56] References Cited

U.S. PATENT DOCUMENTS

| | | | |
|---|---|---|---|
| 852,413 | 5/1907 | Bennett | 433/178 |
| 3,994,068 | 11/1976 | Goshgarian | 433/6 |
| 4,370,134 | 1/1983 | Roberts | 433/172 |
| 4,674,978 | 6/1987 | Acevedo | 433/8 |
| 4,725,230 | 2/1988 | Harima | 433/6 |

FOREIGN PATENT DOCUMENTS

W9675 9/1955 Fed. Rep. of Germany ...... 433/178

*Primary Examiner*—Cary E. O'Connor

[57] ABSTRACT

A retention wire for a tooth which has two ends, one end being adapted to lie against the outside surface of a tooth in front of the back tooth in a plurality of teeth, the other end passing backwardly around the back tooth, then forwardly to the front of the front tooth in said plurality and around it where the second end terminates. The retention wire may include a retention wedge mounted on it comprising a planar sheet of high strength material such as stainless steel, plastic and the like adapted to be placed against the surface of a tooth. The surface which engages the tooth is covered by adhesive material to bond it to a tooth. This adhesive material preferably is in the form of a sheet which is able to bond it both to the wedge and a tooth. The retention wire extends beyond the wedge at both sides thereof. One end is adapted to go around the tooth and engage the inner surface thereof. The other end also extends beyond the side of the wedge where it terminates in a loop which may rest against the gum.

3 Claims, 1 Drawing Sheet

DIRECT BOND RETAINER FOR TEETH

INTRODUCTION

The present invention pertains to a direct bond retainer for teeth, and, more particularly, to a direct bond retainer for teeth which in used in combination with a retention wedge.

BACKGROUND

Patents are known in the prior art which disclose various types of retention wedges adhesively adhered to teeth. Among such patents are the following:

Morgan, U.S. Pat. No. 1,183,396 issued on May 16, 1916, for DENTAL BRIDGEWORK which discloses a bridge having recesses which anchors are located to position the bridge properly in the mouth where it is held by keepers.

Evslin, U.S. Pat. No. 1,393,767 issued on Oct. 18, 1921, for DENTAL BRIDGE CONSTRUCTION which discloses an artificial tooth held between two natural teeth which are provided on their surfaces facing the artificial tooth with grooves in each of which an inlay having a pin vertically secured therein is adhesively held. Each pin fits into a groove on the adjacent surface of the artificial tooth which may be installed by engaging the pins in the vertical grooves and pushing the artificial tooth down until it reaches the gum.

Craig, U.S. Pat. No. 1,698,259 issued on Jan. 8, 1929, for DENTURE which discloses a flange to fit against the side face of a tooth to which a hollow socket is secured.

Newman, U.S. Pat. No. 3,303,565 issued on Feb. 14, 1967, for ORTHODONTIC BRACKETS which discloses a bracket having a back wall contoured to fit the side wall of a tooth to which it is adhesively bonded.

Mueller, U.S. Pat. No. 3,345,745 issued on Oct. 10, 1967, for ORTHODONTIC FASTENING MEANS AND METHOD OF APPLYING THE SAME which discloses a rectangle of pressure sensitive tape or foil to be pressed and held against the side wall of a tooth. The rectangle has an opening in the center through which a metal or synthetic resin portion extends when the tape is secured to a tooth. The metal portion has a head at its outer end with a groove in its outer face through which a strand of synthetic resin or a stainless steel wire can be threaded to assist in holding a series of heads against the side surface of a series of teeth.

Schinhammer, U.S. Pat. No. 4,094,068 issued on Jun. 13, 1978, for ORTHODONTIC BRACKET ASSEMBLY which discloses a bracket having s self adhesive layer on the surface which engages and adheres to the tooth. A series of the brackets is connected to a series of teeth.

Bullock, U.S. Pat. No. 4,180,911 issued on Jan. 1, 1980, for METHOD FOR DIRECT BONDING OF ORTHODONTIC STRUCTURES TO TEETH USING FLUORIDE PRETREATMENT which discloses a mount or bracket secured to teeth by an adhesive mixture with an arch wire extending from mount to mount over a series of teeth.

Kurz, U.S. Pat. No. 4,337,037 issued on Jun. 29, 1982, for FIXED LINGUAL ORTHOPEDIC APPLIANCE FOR MAXILLARY ARCH which discloses a bracket to be applied to teeth by a layer of adhesive applied to the surface thereof which engages the teeth. The bracket has an angular bit plane as a part thereof.

Johnson, U.S. Pat. No. 4,363,624 issued on Dec. 14, 1982, for METHOD OF AFFIXING A DENTAL APPLIANCE which discloses a bracket bonded to the outside surface of each tooth with a high tensile-strength wire attached to the brackets which passes completely around the teeth.

Klepacki, U.S. Pat. No. 4,445,861 issued on May 1, 1984, for DENTURE SUPPORT SYSTEM AND METHOD which discloses a denture framework placed and held against the inner surface of all the teeth by brackets adhesively bonded to the inner surface of the teeth. The planar lower edge of each bracket is at right angles to the surface which engages and is adhered to the inner surface of each tooth in a recess ground into the inner surface of each tooth.

Nicholson, U.S. Pat. No. 4,749,352 issued on Jun. 7, 1988, for METHOD OF BONDING ORTHODONTIC BRACKETS which discloses a wire engaging anchor adhesively secured to the inner surface of each tooth by means of a dimpled or meshed pad having wire engaging anchors on its lower edge, thus enabling two wires to be held by each tooth.

THE JOURNAL OF PROSTHETIC DENTISTRY, volume 53, No. 5, May 1985, pages 655 through 658, discloses etched castings a adjunct to mouth preparation for removable partial dentures.

None of these prior patents nor the article in said JOURNAL discloses the direct bond retention wedge of the invention which comprises a strong, non-resilient wire retainer for teeth which runs along the outer surface of a plurality of rear teeth at the gum line, around the back of the back tooth, a short distance down and in contact with the gum, along the gum substantially parallel to its upper surface, then upwardly in front of the last tooth in that plurality of teeth, around the front surface of the front tooth of that plurality of teeth and finally backwardly over said front tooth in contact with the gum. The wire is used preferably in combination with a planar sheet made of a high strength material such as stainless steel, plastic, and the like adapted to engage the surface of a tooth, means on the inner surface thereof to bond it to that tooth, and a groove in the lower surface to receive and hold the wire. For strength, hygiene and for maximum patient comfort the tooth engaging surfaces of the wedge has a direct bond pad secured thereto which is adapted to bond the wedge to a tooth.

SUMMARY OF THE INVENTION

The invention is a retainer for teeth, particularly a direct bond retention wedge for teeth. The retainer for the teeth comprises a strong, non-resilient wire which has a first end beginning at the gum line on the outside surface of one of the teeth in a plurality of teeth at one side of the mouth, which then runs along the gum line to the rear surface of the back tooth of said plurality, across the back side of said back tooth to the inside surface at the gum line, down the gum a short distance, forwardly along the gum parallel to the teeth for said plurality of teeth, up the gum to the back surface of the front tooth of said plurality of teeth, across the gum to the outside surface of the front tooth of said plurality of teeth and around the outside surface of said front tooth where the second end terminates. The said wire may be supplemented at the outer surface of at least one of the teeth with at least one retention wedge which comprises a planar sheet of high strength material adapted to engage the outer surface of the tooth and means on the inner surface of the wedge to bond it to the tooth. The means for bonding the wedge to the tooth is preferably a direct bond pad material. Each tooth, at least along the sides of the mouth preferably has a wedge secured to its outer surface and preferably each tooth in the mouth has a wedge secured thereto. The retention wedge has a groove in its lower edge opening downwardly for holding the wire which extends from tooth to tooth along at least one side of the mouth, and preferably extends from the rear tooth at one side to the rear tooth on the other side of the mouth.

DETAILED DESCRIPTION OF A PREFERRED EMBODIMENT OF THE INVENTION

Figure 1:
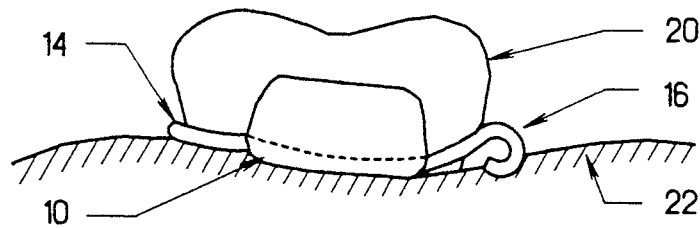
FIG. 1 is a side view showing the outside of a tooth to which a retention wedge is applied with a wire secured to said wedge with a first end looped and resting on the gum adjacent to one edge of the tooth and the second end going around the other edge of the tooth.
Figure 2:
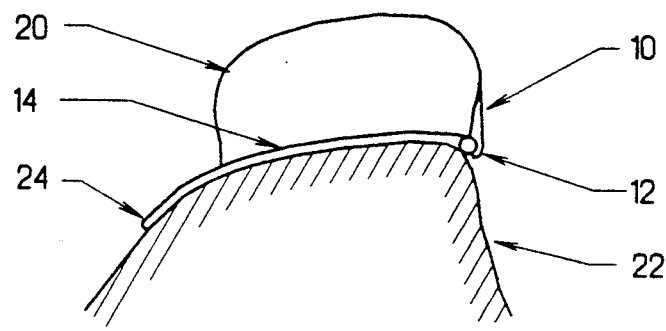
FIG. 2 is a rear view of the rear tooth with the retention wedge in vertical section adhered to its outer surface, the wire being held in the downwardly opening groove in the bottom edge of the wedge, passing around the back surface of the tooth and down the gum in contact therewith.
Figure 3:
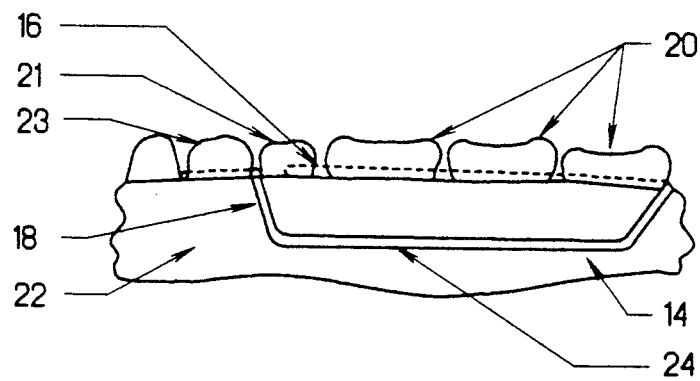
FIG. 3 is an inside view of a row of six teeth including three molars, two premolars and on incisor with the retaining wire beginning at the outside surface of the rear premolar tooth, running along the outside of the three molars backwardly across the last molar to and around its rear side, running downwardly and then forwardly along the inner surface of the gum parallel to the teeth, across the gum in front of the premolar tooth and extending upwardly and across the gum in front of the premolar tooth where it ends.
Figure 4:
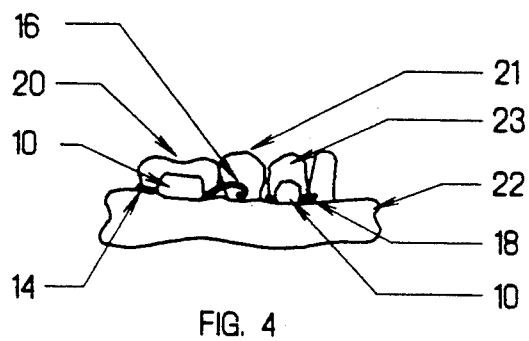
FIG. 4 is a side view from the outside of the third molar, both premolars and one incisor with the first end of the retainer wire starting in a loop at the second premolar, running rearwardly along the gum line on the outside, then forwardly along the gum line on the inside to the space between the premolars, across the gum to the outside and forwardly along the gum across the face of the first premolar where the second end terminates. Wedges 10 are shown on the front surface of the front molar and the second premolar with the retainer wire in a groove at the bottom of each wedge.
Figure 5:
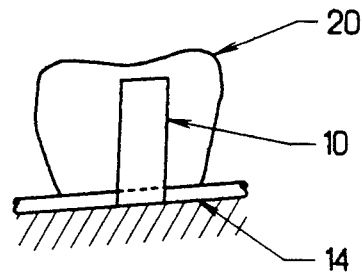
FIG. 5 is a front view of a tooth having the wedge secured to its outer surface with the wire in the groove on it lower edge running across the outer surface of the tooth.

Referring now to the drawing, the invention comprises a retainer wire 14 free of any coil for a plurality of teeth on each side of the mouth which has a first end 16 and a second end 18. The first end 16 begins as a loop at the front of one of the plurality of teeth back of the front tooth of said plurality of teeth, runs along the gum lien 22 to the back of the rear tooth 20 in said plurality, around it and across the gum, down the gum 22 for a short distance, then forwardly as section 24 in contact with the gum 22 parallel to the teeth for the plurality of teeth, then the second end 18 goes up an across the gum 22 in front of the front surface of the front tooth 21 of said plurality of teeth and forwardly along and across the outside surface of the front tooth 21 of said plurality of teeth and forwardly along and across the outside surface of the front tooth 23 of said plurality at the gum line 22 where the second end terminates. The wire 14 may lie in a groove in the bottom surface of at least one wedge 10 in the form of a sheet of high strength material such as stainless steel, plastic and the like against the outside surface of at least one tooth of said plurality of teeth. A downwardly opening groove 12 is provided in the lower edge of the wedge 10 in which the wire 14 may be placed and held, as shown in FIGS. 2, 4 and 5 and it may terminate in a loop 16 which rests against the gum 22, as shown in FIG. 1. The other end 18 of wire 14, after passing behind the rear tooth of said plurality, extends a short distance originate in a loop which rests against the gum 22, as shown in FIGS. 1, 3 and 4. The other end 18 of wire 14, after passing behind the rear tooth of said plurality, extends a short distance down and in contact with the gum 22, then forward parallel to the gum line, along the sum as section 24 for the distance of the plurality of teeth, then up along the gum 22, then forward parallel to the gum 22, then forward parallel to the gum line, along the gum as section 24 for the distance of the plurality of teeth, then up along the gum 22 to and across it at the front of the middle tooth 21, as may be seen in FIG. 3, along the gum at the front of the middle tooth 23, as shown in FIG. 4, and along its outer surface, as shown in FIGS. 3 and 4. When a retention wedge is used in combination with a wire 14, the wire is positioned and held in a downwardly opening groove 12 in the lower surface of the wedge, as seen in FIGS. 1, 2, and 4.

The wedge 10 is intended to become part of the orthodontist's regular supplies and is much more convenient and professional than bonding material the orthodontist must apply to wedges from a supply he otherwise must keep. The wedge will also find use for mixed dentition cases with poor eruption. A person with a cleft palate also greatly appreciates the use of this wedge.

Having thus described and illustrated the invention, what is claimed is:

1. A direct bond retention device for a row of human teeth including a back tooth and a forward tooth, said teeth having outer and inner surfaces, said device comprising a length of strong, non-resilient wire having two ends and no coil in it, one end of said wire being at the said outer surface of a tooth in front of said back tooth, then across the gum, running forwardly along the inner surface of said plurality of teeth, then around said forward tooth where the second end terminates.

2. A direct bond retention device as set forth in claim 1 in which said wire, after passing around the back surface of the back tooth, runs down the gum for a short distance, forwardly parallel to the teeth, upwardly and across the top of the gum between the forward tooth of said plurality of teeth and the next tooth to the front thereof.

3. A direct bond retention wedge for a tooth having a front or outer side or surface, a back side or rear surface, and a front edge and a back edge comprising a sheet of high strength material adapted to engage and to be adhered to the outer surface of a tooth, a groove in an edge of said sheet which, in use, will be near to the gum, a wire in said groove which has forward and rear ends, the rear end of said wire extending rearwardly from a tooth in front of the rear tooth, through said groove in the wedge for a substantial distance and being adapted to extend across the gum at the back edge of said rear tooth onto the rear surface of the tooth and to engage and extend forwardly along it at the gum line, and forward end continuing the forward extension beyond the tooth next to the rear tooth, then across the gum to the front side of the tooth and forwardly along it and having a loop at the forward end which is adapted to rest against the gum.

* * * * *